(12) United States Patent
Chang et al.

(10) Patent No.: US 8,153,401 B2
(45) Date of Patent: Apr. 10, 2012

(54) METHOD FOR DIRECT AMPLIFICATION FROM CRUDE NUCLEIC ACID SAMPLES

(75) Inventors: Chien-Wei Chang, Sunnyvale, CA (US); Dennis Wang, San Mateo, CA (US); Lori K. Hennessy, San Mateo, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 38 days.

(21) Appl. No.: 11/750,316

(22) Filed: May 17, 2007

(65) Prior Publication Data

US 2008/0286772 A1     Nov. 20, 2008

(51) Int. Cl.
*C12Q 1/68* (2006.01)
*C12P 19/34* (2006.01)
*C07H 21/04* (2006.01)

(52) U.S. Cl. ......... 435/91.2; 435/6; 435/91.1; 536/24.3; 536/24.33

(58) Field of Classification Search .................. None
See application file for complete search history.

(56) References Cited

U.S. PATENT DOCUMENTS

| | | | |
|---|---|---|---|
| 5,449,603 A * | 9/1995 | Nielson et al. ............... | 435/6 |
| 5,837,453 A | 11/1998 | Harley et al. | |
| 5,962,665 A * | 10/1999 | Kroeger et al. ............ | 536/23.1 |
| 6,413,747 B1 | 7/2002 | Kato et al. | |
| 7,008,771 B1 * | 3/2006 | Schumm et al. ............ | 435/6 |
| 2007/0015185 A1 * | 1/2007 | Basehore et al. ............ | 435/6 |
| 2008/0233587 A1 | 9/2008 | Wang et al. | |

FOREIGN PATENT DOCUMENTS

EP      1050587 A2     11/2000

OTHER PUBLICATIONS

Forbes et al., "Substances Interfering with Direct Detection of Mycobacterium tuberculosis in Clinical Specimens by PCR: Effects of Bovine Serum Albumin," Journal of Clinical Microbiology, Sep. 1996, vol. 34, No. 9, pp. 2125-2128.*
Abu et al., "Effects of Amplification Facilitators on Diagnostic PCR in the Presence of Blood, Feces, and Meat," Journal of Clinical Microbiology, Dec. 2000, vol. 38, No. 12, pp. 4463-4470.*
Castley et al., "Clinical Applications of Whole-Blood PCR with Real-Time Instrumentation," Clinical Chemistry, 2005, vol. 51, No. 11, pp. 2025-2030.*
"Applied Biosystems, AmpFλSTR. Identifiler, PCR Amplification Kit Users Manual", 2006, p. 1-2, p. 4-34.
Abu Al-Soud et al., "Effects of Amplification Facilitators on Diagnostic PCR in the Presence of Blood, Feces, and Meat", Journal of Clinical Microbiology, Dec. 2000, vol. 38 No. 12, pp. 4463-4470.
International Search Report and Written Opinion PCT/US08/63967, Date Mailed Aug. 21, 2008.
"Two-Step RT-PCR Kit", *product user manual* USB Corporation 2003, pp. 1-17.
U.S. Appl. No. 12/054,174, "Office Action Mailed Oct. 16, 2009", 24 pgs.
Applied Biosystems, "AmpFlstr Identifiler PCR Amplification Kit", *User'Manual* 2006, 1-186.
Kitade, et al., "Effect of DMSO on PCR for *Porphyra yezoensis* (Rhodophyta) gene", *Journal of Applied Physiology*; vol. 15 2003, pp. 557-557.
Sandhu, Effects of the T4 bacteriophage gene 32 product on the efficiency and fidelity of DNA amplification using T4 DNA polymerase, Gene, Elsevier, Amsterdam, NL vol. 144, No. 1, pp. 53-58, 1994.
Olszewski, et al, Application of SSB-like protein from Thermus aquaticus in multiplex PCR of human Y-STR markers identification, Molecular and Cellular Probes, Academic Press, London, GB, vol. 19, No. 3, pp. 203-205, 2005.
Supplementary European Search report, dated Dec. 13, 2010, for EP Application No. 08 75 5756.
Dragon, E. A., "Handling Reagents in the PCR Laboratory", PCR Methods APPL., vol. 3, No. 2, pp. S8-S9, Oct. 1993.
Kreader, C. A., Relief of amplification inhibition in PCR with bovine serum albumin or T4 gene 32 protein, Appl. Environ. Microbiol. vol. 62, No. 3, pp. 1102-1106; abstract p. 1104, paragraph 1; Mar. 1996.
International Search Report of the ISA, mailed 11 Aug 2008, for PCT Application No. PCT/US08/63969.
International Search Report of the ISA, mailed 21 Aug 2008, for PCT Application No. PCT/US08/63967.
Park, S.J., et al., Direct STR Amplification from Whole Blood and Blood- or Saliva-Spotted FTA without DNA Purification, J Forensic Sci, vol. 53, No. 2, pp. 335-341, (2008).
International Preliminary Report on Patentability, mailed on 10-7-10, for PCT Application No. PCT/US08/63969.
Wang, D.Y., et al., Direct amplification of STRs from blood or buccal cell samples, Forensic Sci. Int. Gene. Suppl. (2009), doi:10.1016/j.fsigss.2009.08.069.
Wieczorek, D. and Krenke, B.E. (2009) Direct amplification from buccal and blood samples preserved on cards using the PowerPlex® 16 HS System Profiles in DNA 12(2); [Internet] 2009. www.promega.com/profiles/1202/1202_01.htm.

\* cited by examiner

*Primary Examiner* — Young J Kim

(57) ABSTRACT

The present teachings relate to improved methods, kits, and reaction mixtures for amplifying nucleic acids. In some embodiments a novel direct buffer formulation is provided which allows for the direct amplification of the nucleic acids in a crude sample with minimal sample purification.

21 Claims, No Drawings

METHOD FOR DIRECT AMPLIFICATION FROM CRUDE NUCLEIC ACID SAMPLES

FIELD

The present teachings generally relate to methods of directly amplifying nucleic acids from crude samples.

INTRODUCTION

Rapid and accurate detection of DNA profiles is a key aspect of forensic casework sample analysis. Crude samples such as blood and buccal swabs contain substances that can inhibit the activity of the polymerases used for PCR-based short tandem repeat (STR) typing. Historically, it has been necessary to remove inhibitors and purify DNA before performing downstream enzymatic manipulations such as PCR amplification. Many kinds of DNA isolation and purification methods and kits are commercially available. However, their use adds time and expense.

SUMMARY

The present teachings provide a method of performing a polymerase chain reaction (PCR) comprising; providing a crude sample comprising deoxyribonucleic acid; incubating the crude sample with a direct buffer; removing the eluate from the incubated direct buffer wherein the eluate comprises the deoxyribonucleic acid from the crude sample; and performing a PCR on the deoxyribonucleic acid, 1 wherein the direct buffer comprises at least 5 PCR primer pairs, Tris-HCl at 10-16 mM, KCl at 25-75 mM, dNTPs at 200-400 uM each dNTP, BSA at 160-960 ug/ml, AmpliTaq Gold polymerase at 2U-8U, MgCl2 at 1.25-2.2 mM, and ssb (single-stranded binding protein) of at least 20 ng/ul.

In some embodiments, the direct buffer comprises, Tris-HCl at 10 mM pH 8.3, KCl at 50 mM, dNTPs at 200 uM each dNTP, BSA at 800 ug/ml, AmpliTaq Gold polymerase at 0.16 units/ul, MgCl2 at 1.6 mM, ssb at 60 ng/ul.

In some embodiments, the direct buffer further comprises Sodium Azide at 0.2 percent.

In some embodiments, the ssb is T4 gene 32 protein from bacteriophage T4.

In some embodiments, the present teachings provide a method of determining the identity of a human comprising; providing a crude sample comprising deoxyribonucleic acid from the human; incubating the crude sample with a direct buffer, wherein the direct buffer comprises a plurality of primer pairs, wherein each primer pair flanks a genomic locus containing a short tandem repeat (STR); removing the eluate from the incubated direct buffer, wherein the eluate comprises the deoxyribonucleic acid from the crude sample; performing a PCR on the deoxyribonucleic acids from the crude sample to form a plurality of PCR amplicons, wherein each PCR amplicon has an ascertainable size; and, identifying the human by reference to size of the PCR amplicons, wherein the direct buffer further comprises Tris-HCl at 10-16 mM, KCl at 25-75 mM, dNTPs at 200-400 uM each dNTP, BSA at 160-960 ug/ml, AmpliTaq Gold polymerase at 2U-8U, MgCl2 at 1.25-2.2 mM, and ssb of at least 20 ng/ul.

In some embodiments, the present teachings provide a method of preparing nucleic acids for a downstream enzymatic manipulation comprising; providing a crude sample comprising deoxyribonucleic acid; incubating the crude sample with a direct buffer to form an eluate; removing the eluate from the incubated direct buffer, wherein the eluate comprises the deoxyribonucleic acids from the crude sample; and performing a downstream enzymatic manipulation on the eluate, wherein the direct buffer comprises Tris-HCl at 10-16 mM, KCl at 25-75 mM, dNTPs at 200-400 uM each dNTP, BSA at 160-960 ug/ml, AmpliTaq Gold polymerase at 2U-8U, MgCl2 at 1.25-2.2 mM, and ssb of at least 20 ng/ul.

In some embodiments, the downstream enzymatic manipulation is a PCR.

In some embodiments, the present teachings provide a kit comprising; a plurality of primer pairs, wherein each primer pair flanks a genomic locus containing a short tandem repeat (STR); and, a direct buffer, wherein the direct buffer comprises Tris-HCl at 10-16 mM, KCl at 25-75 mM, dNTPs at 200-400 uM each dNTP, BSA at 160-960 ug/ml, AmpliTaq Gold polymerase at 2U-8U, MgCl2 at 1.25-2.2 mM, and ssb of at least 20 ng/ul.

In some embodiments, the present teachings provide a reaction mixture comprising a direct buffer and a plurality of primer pairs, wherein each primer pair flanks a genomic locus containing a short tandem repeat (STR); and wherein the direct buffer comprises Tris-HCl at 10-16 mM, KCl at 25-75 mM, dNTPs at 200-400 uM each dNTP, BSA at 160-960 ug/ml, AmpliTaq Gold polymerase at 2U-8U, MgCl2 at 1.25-2.2 mM, and ssb at 20-60 ng/ul.

Description of Exemplary Embodiments

In this application, the use of the singular includes the plural unless specifically stated otherwise. In this application, the word "a" or "an" means "at least one" unless specifically stated otherwise. In this application, the use of "or" means "and/or" unless stated otherwise. Furthermore, the use of the term "including," as well as other forms, such as "includes" and "included," is not limiting.

The section headings used herein are for organizational purposes only and are not to be construed as limiting the subject matter described. All documents, or portions of documents, cited in this application, including but not limited to patents, patent applications, articles, books, and treatises are hereby expressly incorporated by reference in their entirety for any purpose. In the event that one or more of the incorporated documents defines a term that contradicts that term's definition in this application, this application controls.

Some Definitions

As used herein, the term "crude sample" refers to a specimen of biological origin suspected of containing nucleic acids, which has not undergone substantial procedures for the isolation of those nucleic acids. For example, a sample of blood is a crude sample. Further, a sample of blood spotted on a paper, such as FTA paper commercially available from Whatman, is a crude sample. A buccal swab of cheek cells is another example of a crude sample. Blood, blood on paper, and buccal swabs are illustrative crude samples. One of skill in the art will recognize an enormous variety of other crude samples whose analysis would be facilitated by the present teachings.

As used herein, the term "direct buffer" refers to a buffer into which a crude sample can be placed. The direct buffer contains primers and enzyme for performing a downstream enzymatic manipulation, such as a polymerase chain reaction (PCR). The direct buffer allows for the liberation of the nucleic acids, and for their amplification from the eluate, without the need for any other purification. Illustrative cycling times and temperatures for PCR can be found in Sambrook et al., Molecular Cloning, $3^{rd}$ Edition. While the present teachings focus on the use of the direct buffer for PCR, it will be appreciated that one of skill in the art can easily employ the direct buffer of the present teachings as a front-end procedure for other types of downstream enzymatic manipulations, for example reverse transcription using a reverse transcriptase, or an oligonucleotide ligation assay using a ligase.

As used herein, the term "eluate" refers to the nucleic acid-containing solution which results from the incubation of the direct buffer with the crude sample.

DETAILED DESCRIPTION

A large number of experiments were performed, varying the respective concentration of each of the ingredients of a desired direct buffer, including Tris-HCl, KCl, dNTPs, BSA, AmpliTaq Gold polymerase, MgCl2, and single stranded binding protein (SSB). These experiments used, for example, humic acid as a mimic for the inhibitors typically present in difficult to analyze samples of biological material, and hence served as an easy to produce proxy for crude samples. The results of these experiments yielded the following formulations.

In some embodiments, the present teachings provide a direct buffer comprising Tris-HCl at 10-16 mM, KCl at 25-75 mM, dNTPs at 200-400 uM each dNTP, BSA at 160-960 ug/ml, AmpliTaq Gold polymerase at 2U-8U, MgCl2 at 1.25-2.2 mM, ssb at 20 ng/ul or higher.

In some embodiments, the direct buffer comprises Tris-HCl at 10 mM pH 8.3, KCl at 50 mM, dNTPs at 200 uM each dNTP, BSA at 800 ug/ml, AmpliTaq Gold polymerase at 0.16 units/ul, MgCl2 at 1.6 mM, and ssb at 60 ng/ul.

In some embodiments, the direct buffer further comprises sodium azide, for example at 0.2 percent.

In some embodiments, the ssb is the T4 gene 32 protein from bacteriophage T4, commercially available from, for example, Ambion, catalog #2424. Generally, the desired concentration of ssb is 20-60 ng/ul. Higher concentrations are possible of course, but a ceiling appears at about 60 ng/ul. In some embodiments, the ssb is present at 60 ng/ul.

The reagents used in the direct buffer are readily available from commercial suppliers. For example, AmpliTaq Gold is commercially available for Applied Biosystems. BSA is commercially available from a variety of sources, for example catalog number 10711454001 from Roche. FTA paper is commercially available from Whatman.

In some embodiments, the direct buffer comprises a plurality of PCR primer pairs. For example, in some embodiments, the direct buffer comprises 5 primer pairs. In some embodiments, the direct buffer comprises 10 primer pairs. In some embodiments, the direct buffer comprises greater than 10 primer pairs. In some embodiments, the direct buffer does not comprise PCR primer pairs, but rather the PCR primer pairs are added to the eluate after the nucleic acids in the crude sample are liberated with the direct buffer.

EXAMPLES

In a first example, blood was applied to FTA paper (Whatman) and air-dried. A 1.2 mm disc punch of FTA paper was made and placed into the direct buffer containing PCR primers from the commercially available Identifiler Human Identity Kit (Applied Biosystems). The disc punch was incubated in the direct buffer for the 10 minutes at room temperature with gentle vortex-mixing occasionally, and the eluate was then transferred into a fresh tube. (Additional dilution of eluate can be made with the PCR master mix if necessary.) PCR was then performed.

In a second example, 100-fold dilutions of blood were made with TE buffer (10 mM Tris-Cl and 0.1 mM EDTA at pH 8.0). 1 ul of diluted blood was used to set up a PCR in the direct buffer.

In a third example, buccal swab samples were collected and placed in 500 ul TE buffer. The resulting suspension was heated at 97C for 5 minutes. 10 ul of the resulting suspension was used to set up a PCR in the direct buffer.

Exemplary Kits in Accordance with Some Embodiments of the Present Teachings

In some embodiments, the present teachings also provide kits designed to expedite performing certain methods. In some embodiments, kits serve to expedite the performance of the methods of interest by assembling two or more components used in carrying out the methods. In some embodiments, kits may contain components in pre-measured unit amounts to minimize the need for measurements by end-users. In some embodiments, kits may include instructions for performing one or more methods of the present teachings. In certain embodiments, the kit components are optimized to operate in conjunction with one another.

While the present teachings have been described in terms of these exemplary embodiments and experimental data, the skilled artisan will readily understand that numerous variations and modifications of these exemplary embodiments are possible without undue experimentation. All such variations and modifications are within the scope of the current teachings.

Thus, in some embodiments, the present teachings provide a kit comprising; a plurality of primer pairs, wherein each primer pair flanks a genomic locus containing a short tandem repeat (STR); and, a direct buffer, wherein the direct buffer comprises Tris-HCl at 10-16 mM, KCl at 25-75 mM, dNTPs at 200-400 uM each dNTP, BSA at 160-960 ug/ml, AmpliTaq Gold polymerase at 2U-8U, MgCl2 at 1.25-2.2 mM, and ssb of at least 20 ng/ul. Such a kit can be used, for example, in the identification of an organism such as a human by the collection of polymorphic microsatellites analyzed, using for example capillary electrophoresis. Illustrative procedures for performing such human identification can be found for example in the Identifiler HID kit, commercially available from Applied Biosystems, as well as U.S. Pat. Nos. 6,221, 598, 6,479,235, 5,843,660, and 7,008,771. In some embodiments, the kits, and methods and reaction mixtures provided by the present teachings can be used with procedures for multiplexed PCR of degraded samples, as found for example in WO05054515 to Dimsoski and Woo.

In some embodiments, the direct buffer in the kit comprises, Tris-HCl at 10 mM pH 8.3, KCl at 50 mM, dNTPs at 200 uM each dNTP, BSA at 800 ug/ml, AmpliTaq Gold polymerase at 0.16 units/ul, MgCl2 at 1.6 mM, and ssb at 60 ng/ul.

In some embodiments, the direct buffer in the kit further comprises Sodium Azide at 0.2 percent.

In some embodiments, the ssb in the kit is the T4 gene 32 protein from bacteriophage T4.

The invention claimed is:

1. A method of performing a polymerase chain reaction (PCR) comprising;
   providing a crude sample comprising deoxyribonucleic acid;
   incubating the crude sample with a direct buffer to form a nucleic acid-containing solution; and
   performing a polymerase chain reaction (PCR) on said nucleic acid-containing solution, wherein the direct buffer comprises at least 5 PCR primer pairs, Tris-HCl at 10-16 mM, KCl at 50-75 mM, dNTPs at 200-400 uM each dNTP, BSA at 800-960 ug/ml, AmpliTaq Gold polymerase at 2U-8U, MgCl2 at 1.6-2.2 mM, and single-stranded binding protein (ssb) of at least 20 ng/ul.

2. The method according to claim 1, wherein the direct buffer comprises, Tris-HCl at 10 mM pH 8.3, KCl at 50 mM, dNTPs at 200 uM each dNTP, BSA at 800 ug/ml, AmpliTaq Gold polymerase at 0.16 units/ul, MgCl2 at 1.6 mM, ssb at 60 ng/ul.

3. The method according to claim 2, wherein the direct buffer further comprises Sodium Azide at 0.02 percent.

4. The method according to claim 2, wherein the ssb is T4 gene 32 protein from bacteriophage T4.

5. A method of determining the identity of a human comprising:
providing a crude sample comprising deoxyribonucleic acid from the human;
incubating the crude sample with a direct buffer to form a nucleic acid-containing solution, wherein the direct buffer comprises a plurality of primer pairs,
wherein each primer pair flanks a genomic locus containing a short tandem repeat (STR);
wherein the solution comprises the deoxyribonucleic acid from the crude sample;
performing a PCR on the deoxyribonucleic acids from the crude sample to form a plurality of PCR amplicons, wherein each PCR amplicon has an ascertainable size; and,
identifying the human by reference to size of the PCR amplicons, wherein the direct buffer further comprises Tris-HCl at 10-16 mM, KCl at 50-75 mM, dNTPs at 200-400 uM each dNTP, BSA at 800-960 ug/ml, AmpliTaq Gold polymerase at 2U-8U, MgCl2 at 1.6-2.2 mM, and ssb of at least 20 ng/ul.

6. The method according to claim 5, wherein the direct buffer comprises, Tris-HCl at 10 mM pH 8.3, KCl at 50 mM, dNTPs at 200 uM each dNTP, BSA at 800 ug/ml, AmpliTaq Gold polymerase at 0.16 units/ul, MgCl2 at 1.6 mM, and ssb at 60 ng/ul.

7. The method according to claim 6, wherein the direct buffer further comprises Sodium Azide at 0.02 percent.

8. The method according to claim 6 wherein the ssb is T4 gene 32 protein from bacteriophage T4.

9. A method of preparing nucleic acids for an enzymatic manipulation comprising:
providing a crude sample comprising deoxyribonucleic acid;
incubating the crude sample with a direct buffer to form a nucleic acid-containing solution;
wherein the solution comprises the deoxyribonucleic acids from the crude sample; and wherein the direct buffer comprises Tris-HCl at 10-16 mM, KCl at 50-75 mM, dNTPs at 200-400 uM each dNTP, BSA at 800-960 ug/ml, AmpliTaq Gold polymerase at 2U-8U, MgCl2 at 1.6-2.2 mM, and ssb of at least 20 ng/ul, and said nucleic acid-containing solution is used in the enzymatic manipulation.

10. The method according to claim 9 wherein the enzymatic manipulation is a PCR.

11. The method according to claim 9 wherein the direct buffer comprises, Tris-HCl at 10 mM pH 8.3, KCl at 50 mM, dNTPs at 200 uM each dNTP, BSA at 800 ug/ml, AmpliTaq Gold polymerase at 0.16 units/ul, MgCl2 at 1.6 mM, and ssb at 60 ng/ul.

12. The method according to claim 11 wherein the direct buffer further comprises Sodium Azide at 0.02 percent.

13. The method according to claim 11 wherein the ssb is T4 gene 32 protein from bacteriophage T4.

14. A kit for analysis of a crude sample comprising:
a plurality of primer pairs, wherein each primer pair flanks a genomic locus containing a short tandem repeat (STR); and, a direct buffer, wherein the direct buffer comprises Tris-HCl at 10-16 mM, KCl at 50-75 mM, dNTPs at 200-400 uM each dNTP, BSA at 800-960 ug/ml, AmpliTaq Gold polymerase at 2U-8U, MgCl2 at 1.6-2.2 mM, and ssb of at least 20 ng/ul.

15. The kit according to claim 14 wherein the direct buffer comprises, Tris-HCl at 10 mM pH 8.3, KCl at 50 mM, dNTPs at 200 uM each dNTP, BSA at 800 ug/ml, AmpliTaq Gold polymerase at 0.16 units/ul, MgCl2 at 1.6 mM, and ssb at 60 ng/ul.

16. The kit according to claim 15 wherein the direct buffer further comprises Sodium Azide at 0.02 percent.

17. The kit according to claim 15 wherein the ssb is T4 gene 32 protein from bacteriophage T4.

18. A reaction mixture comprising a direct buffer and a plurality of primer pairs, wherein each primer pair flanks a genomic locus of a crude sample containing a short tandem repeat (STR); and wherein the direct buffer comprises Tris-HCl at 10-16 mM, KCl at 50-75 mM, dNTPs at 200-400 uM each dNTP, BSA at 800-960 ug/ml, AmpliTaq Gold polymerase at 2U-8U, MgCl2 at 1.6-2.2 mM, and ssb of at least 20 ng/ul.

19. The reaction mixture according to claim 18 wherein the direct buffer comprises, Tris-HCl at 10 mM pH 8.3, KCl at 50 mM, dNTPs at 200 uM each dNTP, BSA at 800 ug/ml, AmpliTaq Gold polymerase at 0.16 units/ul, MgCl2 at 1.6 mM, and ssb at 60 ng/ul.

20. The reaction according to claim 19 wherein the direct buffer further comprises Sodium Azide at 0.02 percent.

21. The reaction mixture according to claim 19, wherein the ssb is T4 gene 32 protein from bacteriophage T4.

* * * * *

UNITED STATES PATENT AND TRADEMARK OFFICE
CERTIFICATE OF CORRECTION

| | | |
|---|---|---|
| PATENT NO. | : 8,153,401 B2 | Page 1 of 1 |
| APPLICATION NO. | : 11/750316 | |
| DATED | : April 10, 2012 | |
| INVENTOR(S) | : Lori K. Hennessy, Dennis Y. Wang and Chien-Wei Chang | |

It is certified that error appears in the above-identified patent and that said Letters Patent is hereby corrected as shown below:

On the Title Page, item [56], Column 2, Lines 1-2:
    Applied Biosystems, AmpFΛSTR. Identifer, PCT Amplification Kit Users Manual, 2006, 1-2, p. 4-34.
        delete "AmpFΛSTR" and insert --AmpFℓSTR--

On the Title Page, item [56], Column 2, Lines 13-16
    Kitade, et al., "Effect of DMSO on PCR for Porphyra yezoensis (Rhodophyta) gene", Journal of Applied Physiology; vol 15 2003, pages 557-557.
        delete "pages 557-557" and insert --pages 555-557--

In the Claims:
    Column 5, Line 47, Claim 9
        delete "comprising:" and insert --comprising;--

Signed and Sealed this
Fourteenth Day of May, 2013

Teresa Stanek Rea
*Acting Director of the United States Patent and Trademark Office*